US009846132B2

(12) United States Patent
Bakeman et al.

(10) Patent No.: US 9,846,132 B2
(45) Date of Patent: Dec. 19, 2017

(54) SMALL-ANGLE SCATTERING X-RAY METROLOGY SYSTEMS AND METHODS

(71) Applicant: KLA-Tencor Corporation, Milpitas, CA (US)

(72) Inventors: Michael S. Bakeman, Union City, CA (US); Andrei V. Shchegrov, Campbell, CA (US); Ady Levy, Sunnyvale, CA (US); Guorong V. Zhuang, San Jose, CA (US); John J. Hench, Los Gatos, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 256 days.

(21) Appl. No.: 14/515,322

(22) Filed: Oct. 15, 2014

(65) Prior Publication Data

US 2015/0110249 A1 Apr. 23, 2015

Related U.S. Application Data

(60) Provisional application No. 61/893,341, filed on Oct. 21, 2013.

(51) Int. Cl.
*G01N 23/00* (2006.01)
*G01N 23/201* (2006.01)
*G01N 33/00* (2006.01)

(52) U.S. Cl.
CPC ... *G01N 23/201* (2013.01); *G01N 2033/0095* (2013.01)

(58) Field of Classification Search
CPC .................................................. G01N 23/201
See application file for complete search history.

(56) References Cited

U.S. PATENT DOCUMENTS

| 5,859,424 | A | 1/1999 | Norton et al. |
| 6,816,570 | B2 | 11/2004 | Janik et al. |
| 6,895,075 | B2 | 5/2005 | Yokhin et al. |
| 6,972,852 | B2 | 12/2005 | Opsal et al. |
| 7,929,667 | B1 | 4/2011 | Zhuang et al. |
| 2005/0282300 | A1* | 12/2005 | Yun ................ G01N 23/2252 438/14 |

(Continued)

OTHER PUBLICATIONS

"Int'l Application Serial No. PCT/US2014/061573, Search Report & Written Opinion dated Jan. 27, 2015", 12 pgs.

(Continued)

*Primary Examiner* — Dani Fox
(74) *Attorney, Agent, or Firm* — Kwan & Olynick, LLP

(57) ABSTRACT

Disclosed are apparatus and methods for performing small angle x-ray scattering metrology. This system includes an x-ray source for generating x-rays and illumination optics for collecting and reflecting or refracting a portion of the generated x-rays towards a particular focus point on a semiconductor sample in the form of a plurality of incident beams at a plurality of different angles of incidence (AOIs). The system further includes a sensor for collecting output x-ray beams that are scattered from the sample in response to the incident beams on the sample at the different AOIs and a controller configured for controlling operation of the x-ray source and illumination optics and receiving the output x-rays beams and generating an image from such output x-rays.

13 Claims, 9 Drawing Sheets

(56) References Cited

U.S. PATENT DOCUMENTS

| | | |
|---|---|---|
| 2007/0224518 A1 | 9/2007 | Yokhin et al. |
| 2008/0137810 A1 | 6/2008 | Liu et al. |
| 2011/0080585 A1 | 4/2011 | Rabello et al. |
| 2011/0280530 A1 | 11/2011 | Verman et al. |
| 2013/0155406 A1 | 6/2013 | Den Boef |

OTHER PUBLICATIONS

Bakeman, Michael S. et al., "Model Building and Analysis Engine for Combined X-Ray and Optical Metrology", U.S. Appl. No. 13/935,275, filed Jul. 3, 2013, 53 pgs.

Huang, Xiaojing et al., "11 nm Hard X-Ray Focus from a Large-Aperture Multilayer Laue Lens", Scientific Reports, 3:3562, Dec. 20, 2013, 5 pgs.

Sunday, Daniel F. et al., "Three-Dimensional X-Ray Metrology for Block Copolymer Lithography Line-Space Patterns", Journal of Micro/Nanolithography, MEMS, and MOEMS, SPIE Digital Library, 12(3), Retrieved from the Internet: <http://nanolithography.spiedigitallibrary.org/, Accessed on Oct. 8, 2014, 2013, 8 pgs.

Vestli, K. et al., "Optimization of Multilayer Reflectivity and Bandpass for Soft to Hard Xray Applications", Review of Scientific Instruments, 67, 3356, Retrieved Online: <http://nanolithography.spiedigitallibrary.org/>, Accessed on Oct. 8, 2014, 1996, 6 pgs.

Zhang, Guorong V. et al., "High Brightness Liquid Droplet X-Ray Source for Semiconductor Metrology", U.S. Appl. No. 14/304,329, filed Jun. 13, 2014, 46 pgs.

\* cited by examiner

SMALL-ANGLE SCATTERING X-RAY METROLOGY SYSTEMS AND METHODS

CROSS-REFERENCE TO RELATED APPLICATIONS

This application claims the benefit of prior application U.S. Provisional Application No. 61/893,341, filed 21 Oct. 2013 by Michael S. Bakeman et al., which application is herein incorporated by reference in its entirety for all purposes.

TECHNICAL FIELD OF THE INVENTION

The present invention relates generally to methods and systems for semiconductor metrology and, more specifically, to using x-ray illumination.

BACKGROUND

Photolithography or optical lithography systems used in the manufacture of integrated circuits have been around for some time. Such systems have proven extremely effective in the precise manufacturing and formation of very small details in the product. In some photolithography systems, a circuit image is written on a substrate by transferring a pattern via a light or radiation beam (e.g., UV or ultraviolet light). For example, the lithography system may include a light or radiation source that projects a circuit image through a reticle and onto a silicon wafer coated with a material sensitive to irradiation, e.g., photoresist. The exposed photoresist typically forms a pattern that after development masks the layers of the wafer during subsequent processing steps, as for example deposition and/or etching.

Due to the large scale of circuit integration and the decreasing size of semiconductor devices, the reticles and fabricated devices have become increasingly sensitive to critical dimension (CD) variations, as well as other critical parameter variations such as film thickness and composition, etc. These variations, if uncorrected, can cause the final device to fail to meet the desired performance due to electrical timing errors. Even worse, these errors can cause final devices to malfunction and adversely affect yield.

In one metrology technique, critical dimension is measured by scanning electron microscope CD-SEM images at each target location on the wafer and examining each image for pattern quality. This technique is time consuming (e.g., several hours). Other techniques have their own disadvantages.

Additionally, buried defects can be difficult to detect with certain metrology tools. Traditionally, the only way to know the size, distribution and location of buried voids, for example, is by using destructive methods such as Focused Ion Beam (FIB) cross-sectioning techniques. Although these techniques can help verify the existence of voids, the sample is destroyed during the analysis. This technique is expensive for integrated circuit manufacturers since it means sacrificing product samples from the product line and often results in wasting product found to have no significant defects. Furthermore, FIB techniques are time consuming, which can cause downtime of the product line production. This increased downtime can be an especially big problem if numerous scans on numerous wafers are needed to ensure void-free processing.

In view of the foregoing, improved apparatus and techniques for determining structure or process parameters of a printed pattern are desired.

SUMMARY

The following presents a simplified summary of the disclosure in order to provide a basic understanding of certain embodiments of the invention. This summary is not an extensive overview of the disclosure and it does not identify key/critical elements of the invention or delineate the scope of the invention. Its sole purpose is to present some concepts disclosed herein in a simplified form as a prelude to the more detailed description that is presented later.

In one embodiment, a semiconductor metrology system is disclosed. This system includes an x-ray source for generating x-rays and illumination optics for collecting and reflecting or refracting a portion of the generated x-rays towards a particular focus point on a semiconductor sample in the form of a plurality of incident beams at a plurality of different angles of incidence (AOIs). The system further includes a sensor for collecting output x-ray beams that are scattered from the sample in response to the incident beams on the sample at the different AOIs and a controller configured for controlling operation of the x-ray source and illumination optics and receiving the output x-rays beams and generating an image from such output x-rays.

In a specific implementation, the illumination optics and sensor are arranged to form a transmission small-angle x-ray scattering (T-SAXS) system. In another embodiment, the illumination optics and sensor are arranged to form a grazing incident small-angle x-ray scattering (GI-SAXS) system. In one aspect, the illumination optics comprise a plurality of grazing incident reflecting mirrors, and the grazing incident reflecting mirrors comprise sets of one or more grazing incident reflecting mirrors having multiple layers and that are arranged and sized to collect and reflect specific solid angles of the generated x-rays. In a further aspect, each grazing incident reflecting mirror has a curved shape and the grazing incident reflecting mirrors together form nested rings so that each ring collects and reflects a different range of AOI's. In yet another aspect, the grazing incident reflecting mirrors together are arranged in a plurality of positions in a plurality of nested rings so that the grazing incident reflecting portions in each ring together collect and reflect a different range of AOI's than grazing incident reflecting portions in other rings. In another example, the multiple layers of the grazing incident reflecting mirrors each have a plurality of portions having different periods, which is each selected to meet the Bragg condition so that the incident beams that are collected and reflected by all the portions are directed towards the particular focus point.

In another embodiment, the illumination optics are configured to reflect or refract the plurality of incident beams simultaneously towards the sample at the different angles of incidence (AOIs). In another specific implementation, the x-ray source comprises an anode that is doped with one or more elements. In other example embodiments, the illumination optics comprise multilayer Laue lenses having multiple layer spacings having a period for refracting the generated x-rays as the incident beams towards the particular focus point at the different AOIs, multiple Fresnel zone plate lenses that are arranged to produce the incident beams towards the particular focus point at the different AOIs, polycapillary optics that are arranged to produce the incident beams towards the particular focus point at the different AOIs, or a plurality of curved crystals having a plurality of different lattice plane spacings that are positioned to result in the incident beams at the different AOIs.

In another specific implementation, the illumination optics comprise a multi-AOI illuminator for collecting and reflecting or refracting the incident beams towards the particular focus point on the sample at the different AOIs and a plurality of differently sized apertures placed in a path of the incident beams to control a spot size and/or beam divergence for the different AOIs. In a further aspect, at least some of the apertures each include a single crystal that is bonded to edges of such aperture. In another aspect, each of the differently sized apertures are arranged to be dynamically positioned in a path of the incident beams or output x-ray beams, and the multi-AOI illuminator is arranged to cause the incident beams to have an upper limit of a first divergence and first spot size and the differently sized apertures are sized and shaped to block portions of the incident beams so as to achieve lower divergence than the first divergence and smaller spots sizes than the first spot size for particular target structures.

In an alternative embodiment, the invention pertains to a method. The method includes (i) illuminating a focus point of a semiconductor sample with a plurality of incident x-ray beams at a plurality of different angles of incidence (AOIs), wherein the different AOIs are produced simultaneously on the focus point of the sample, (ii) collecting output x-ray beams that are scattered from the sample in response to the incident beams on the sample at the different AOIs, and (iii) generating an image based on the output x-ray beams.

These and other aspects of the invention are described further below with reference to the figures.

DETAILED DESCRIPTION OF EXAMPLE EMBODIMENTS

In the following description, numerous specific details are set forth in order to provide a thorough understanding of the present invention. The present invention may be practiced without some or all of these specific details. In other instances, well known process operations have not been described in detail to not unnecessarily obscure the present invention. While the invention will be described in conjunction with the specific embodiments, it will be understood that it is not intended to limit the invention to the embodiments.

Certain embodiments of the present invention provide a scatterometry apparatus with small angle x-ray scattering (SAXS) capabilities. This system may include a high brightness x-ray source coupled with a high efficiency x-ray illumination system with improved measurement capabilities. A SAXS system is capable of measuring geometric parameters in semiconductor structures such as overlay, pitch, critical dimensions (CD), height, side wall angle (SWA), line-width roughness (LWR), line-edge roughness (LER), pitch walk, etc. The measured features can also be smaller than 10 nm. In addition, the high energy nature of x-ray radiation allows for the penetration of x-rays into optically opaque thin films, buried structures, high-aspect ratio structures and devices containing many thin film layers.

Figure 1:
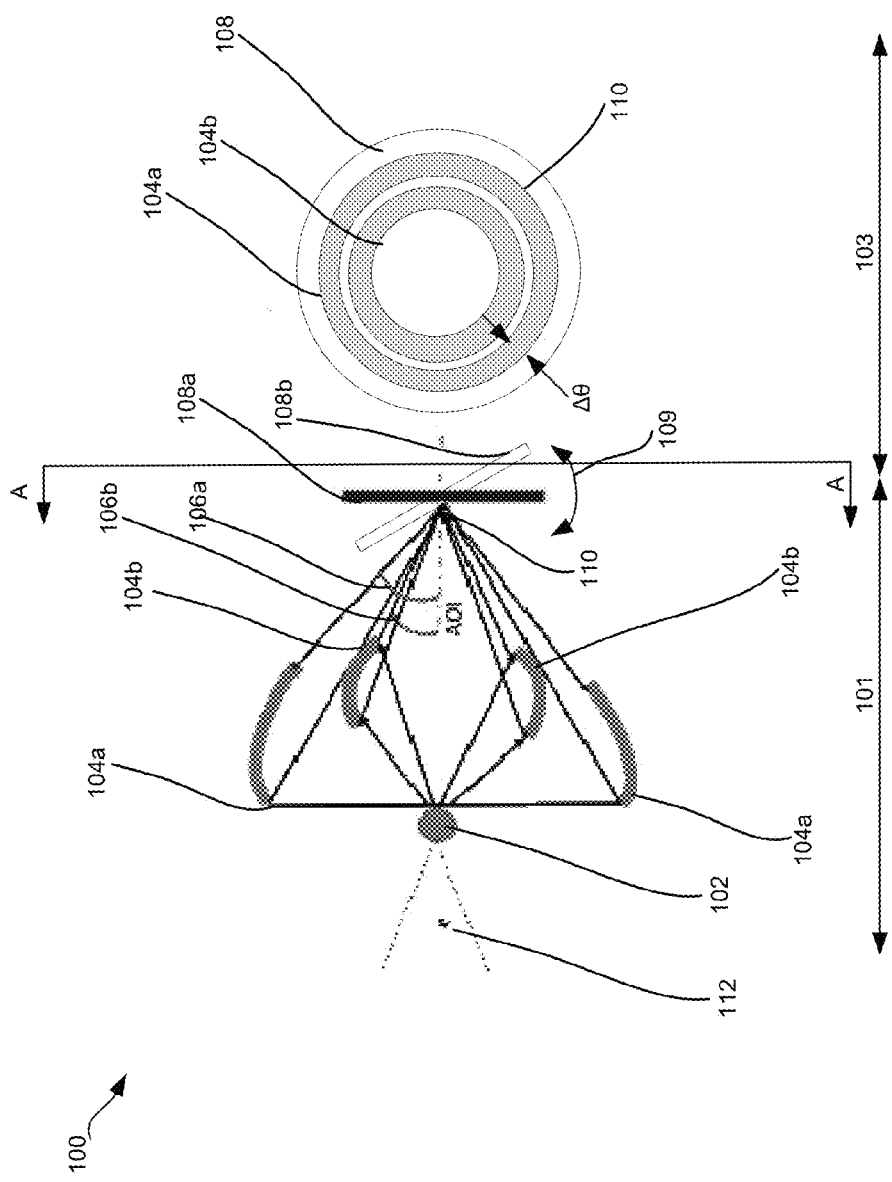
FIG. 1 is a diagrammatic side view and bottom view of a transmission small angle x-ray scattering (T-SAXS) illumination system in accordance with one embodiment of the present invention.

FIG. 1 is a diagrammatic side view and bottom view of a transmission small angle x-ray scattering (T-SAXS) illumination system 100 in accordance with one embodiment of the present invention. The left side of the drawing contains a side view 101, while the right side of the drawing contains a bottom view 103 from perspective line A-A of the side view 101. As shown, an excitation electron beam 112 is directed towards an x-ray anode 102, which then emits x-rays towards a sample 108a. This sample 108a is oriented with its measurement surface positioned vertically.

The x-rays are reflected from a plurality of grazing incidence X-ray mirrors (e.g., 104a and 104b) towards a same point 110 on the sample 108. The side view 101 shows a cutout portion of each incident mirror, while the bottom view 103 shows the entire enclosed grazing mirror cylinder. In the illustrated arrangement, each grazing incident mirror forms a slopped or curved cylinder shape, and together the grazing mirrors form nested cylinders. Alternatively, mirrors could be spaced around portions of concentric rings, rather than forming complete rings.

The grazing mirrors reflect x-rays to the sample at specific associated angles of incidence (AOI's 106a and 106b). For instance, grazing mirror 104a forms x-rays with AOI 106a, while grazing mirror 104b forms x-rays with AOI 106b with respect to a normal axis for sample 108a.

The grazing mirrors can be sized and arranged to meet the Bragg relation and collect and reflect x-rays in $2\pi$ (or $\phi$) portions that are $\Delta\theta$ wide as shown in the bottom view 103. That is, each collection optics (e.g., grazing mirror) may be positioned and sized to collect a particular solid angle of the X-rays. Only light that is produced in a particular cone is going to be incident on each grazing mirror.

For achieving a high X-ray throughput, a set of grazing incident mirrors can collect photons within a large $\Delta\theta$ over $\phi$ ($2\pi$). Alternatively, multiple sets of grazing incident mirrors focusing mirrors can be used to collect a portion of the x-rays from the source and focus them onto the same measurement spot on the sample with the sets of mirrors having multiple AOIs. In this way, SAXS can be performed with multiple measurements at different AOIs being performed in parallel.

Although multiple grazing mirrors can achieve multiple, simultaneous AOI's of X-rays incident on the sample, the sample 108a can also optionally be tilted to achieve further AOI's. Different tilt positions in directions 109 for the sample will result in different AOI's with respect to the specific x-rays that are reflected from the grazing mirrors. For instance, sample 108b is shown at a second tilt position with respect to first position sample 108a. Tilting of the sample is unnecessary, however, and multiple AOI's can be achieved on the sample without tilting of the sample.

The x-ray beams may be collimated or focused and/or monochromatized by the illumination x-ray optics and then incident on the sample. One of the ways to focus and monochromatize an x-ray beam is through the use of multilayer mirrors. The mirrors are based upon the principle of constructive interference of waves at the interface of a stack of thin layers of alternating materials, for example, in the form of grazing mirrors.

Figure 2:
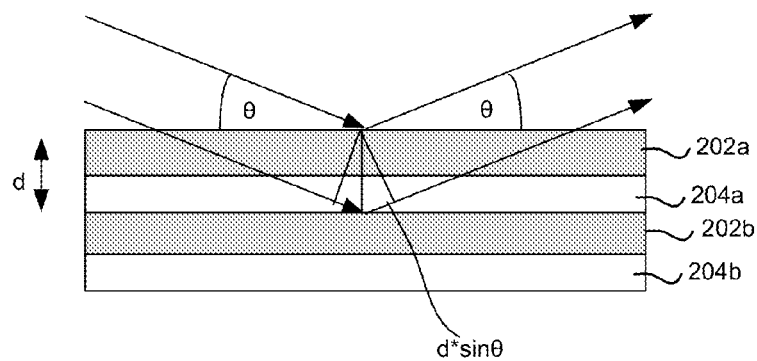
FIG. 2 is a simplified diagrammatic representation of a multilayer stack.

FIG. 2 is a simplified diagrammatic representation of a multilayer stack having alternating first layers (e.g., 202a and 202b) formed from a first material and second layers (e.g., 204a and 204b) formed from a second material that differs from the first material. The period d of the multilayer thickness is designed to satisfy Bragg's condition: $2d \sin \theta = n\lambda$, where $\lambda$ is the wavelength of the X-ray to be reflected and $\theta$ is the angle of incidence on the mirror. Multilayer mirrors can be used at much larger incidence angles in the soft x-ray (6-13.5 nm) and EUV (13.5~20 nm) regimes. Usually, the period of a multilayer needs to be comparable to $\lambda$ in order to satisfy the Bragg condition. In general, the angle acceptance range of the mirrors can be controlled for a particular wavelength by the multilayer spacing d. Additionally, the geometrical distances of the mirrors from the source are selected to satisfy the Bragg condition. Different mirror compositions and configurations can be simulated at different distances and angles from the source, and then the different Bragg angles can be determined, as well as simulating whether the mirrors are efficient at the particular spatial placements. In another example, given a source illumination property and particular mirror composition (materials and d), the areas outside the source that satisfy the Bragg conditions can be simulated, and the mirrors can be placed at such areas. Typically, there will be a very small number of angular acceptance ranges (e.g., $\Delta\theta$) for which a strong reflectivity signal is achieved for a particular mirror and x-ray source.

The grazing mirrors can be designed for maximum flux, rather than resolution. For x-ray mirrors that are suitable for an x-ray energy range of about 7.5 to 43 keV, for example, the multilayer mirror d can be 1.5 nm~6 nm, and $\Gamma$ (ratio of bottom layer thickness/period) can be 0.2~0.5. The number of periods N can be 1-400, which is a trade-off between peak reflectivity and spectral bandwidth $\Delta E/E$. In the multilayer stack, the bottom layer is designated as material 2/material group 2, and top layer as material 1/material group 1. Both the top layer and the bottom layer can have of composition of either pure elements or compound materials. By way of example, the material for the top layer can be Ni, Cr, Cu, Zn, Mo, Ru, Rd, Rh, V, Co, WSi2, GeO2, Al2O3, or MgO, and the material for bottom layer can be B, Mg, C, Si, B4C, or BN.

For certain applications, the x-ray energies of interest are from about 15 keV to 30 keV with $\lambda$ between about 0.83 Å to 0.41 Å, which are typical energies and wavelengths or "hard" x-rays that may be used for semiconductor scatterometry targets. When a transmission type analysis is to be used, a significant amount of the incident x-rays need to penetrate the sample and have a relatively high energy to do so. Accordingly, 15 keV may represent a minimal energy for the x-rays in the T-SAXS embodiment. However, x-ray energies above 30 keV are also contemplated, and the range 15 keV to 30 keV is merely an exemplary range.

Certain normal incidence multilayer mirrors can also be limited in this regime due to limits in the multilayer period, which can be limited to 3~4 nm. Given such a multilayer stack period, the reflectivity and angle of incidence at which such reflectivity can be reached can be simulated and tabulated, for example, for 30 keV x-rays as shown in Table 1 below. In Table 1, F is the ratio of bottom layer thickness/period; N is the number of periods, the grazing incident angle is with respect to multilayer surface (instead of surface normal); and the substrate is Si. These simulations show that in the hard x-ray regime multilayer mirrors only work for grazing angles that are less than about 1°, but with very high efficiency (55%-90%). Embodiments of the present invention are not limited to the exemplary multilayer materials and configurations of Table 1.

TABLE 1

Multilayer for 30 keV X-ray mirror

| Multilayer Material | Period d (nm) | Γ | N | Grazing incident angle(°) | Reflec. (%) |
|---|---|---|---|---|---|
| Mo/C | 4 | 0.6 | 200 | 0.3 | 55 |
| W/Si | 4 | 0.35 | 200 | 0.3 | 80 |
| Ni/C | 4 | 0.6 | 200 | 0.3 | 82 |
| Ni/BN | 4 | 0.6 | 200 | 0.3 | 82 |
| W/C | 5 | 0.7 | 200 | 0.5 | 70 |
| W/C | 4 | 0.3 | 200 | 0.5 | 85 |
| WSi2/C | 4 | 0.5 | 200 | 0.3 | 90 |
| WSi2/C | 5 | 0.75 | 200 | 0.5 | 90 |

Figure 3:
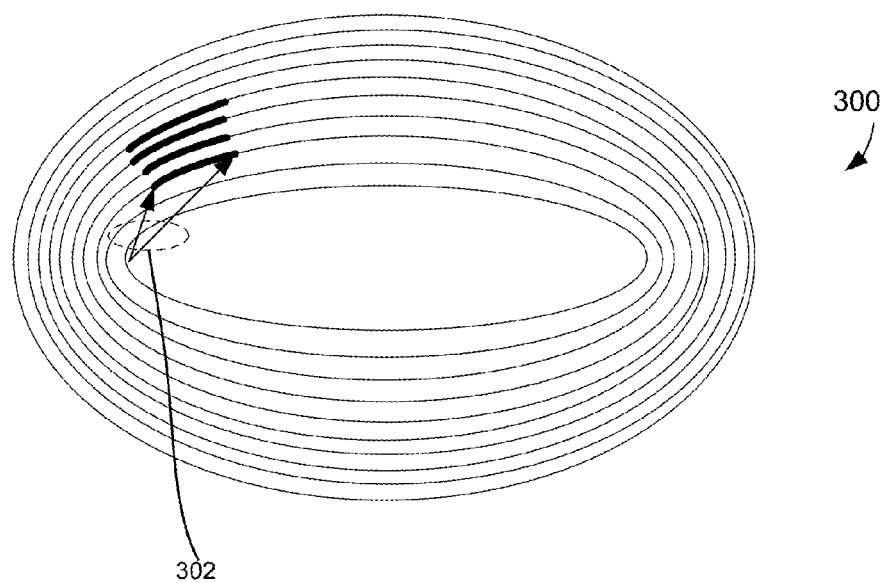
FIG. 3 is a representation of a multilayer mirror in accordance with one specific implementation of the present invention.

FIG. 3 is a representation of a multilayer mirror 300 in accordance with one specific implementation of the present invention. As shown, different portions of the multiple layers, along the ring, of the mirror may have varying thicknesses, depending on its relative placement with respect to the incident x-rays 302. That is, each ray of the x-ray bundle will have a different angle (e.g., $\Delta\theta$) with respect to the multilayer portion upon which it is incident, so each optics portion may have a corresponding d value to meet the Bragg condition so that all the x-rays that hit and are reflected from the multilayer mirror 300 will hit a same focus point with respect to the target.

Figure 4:
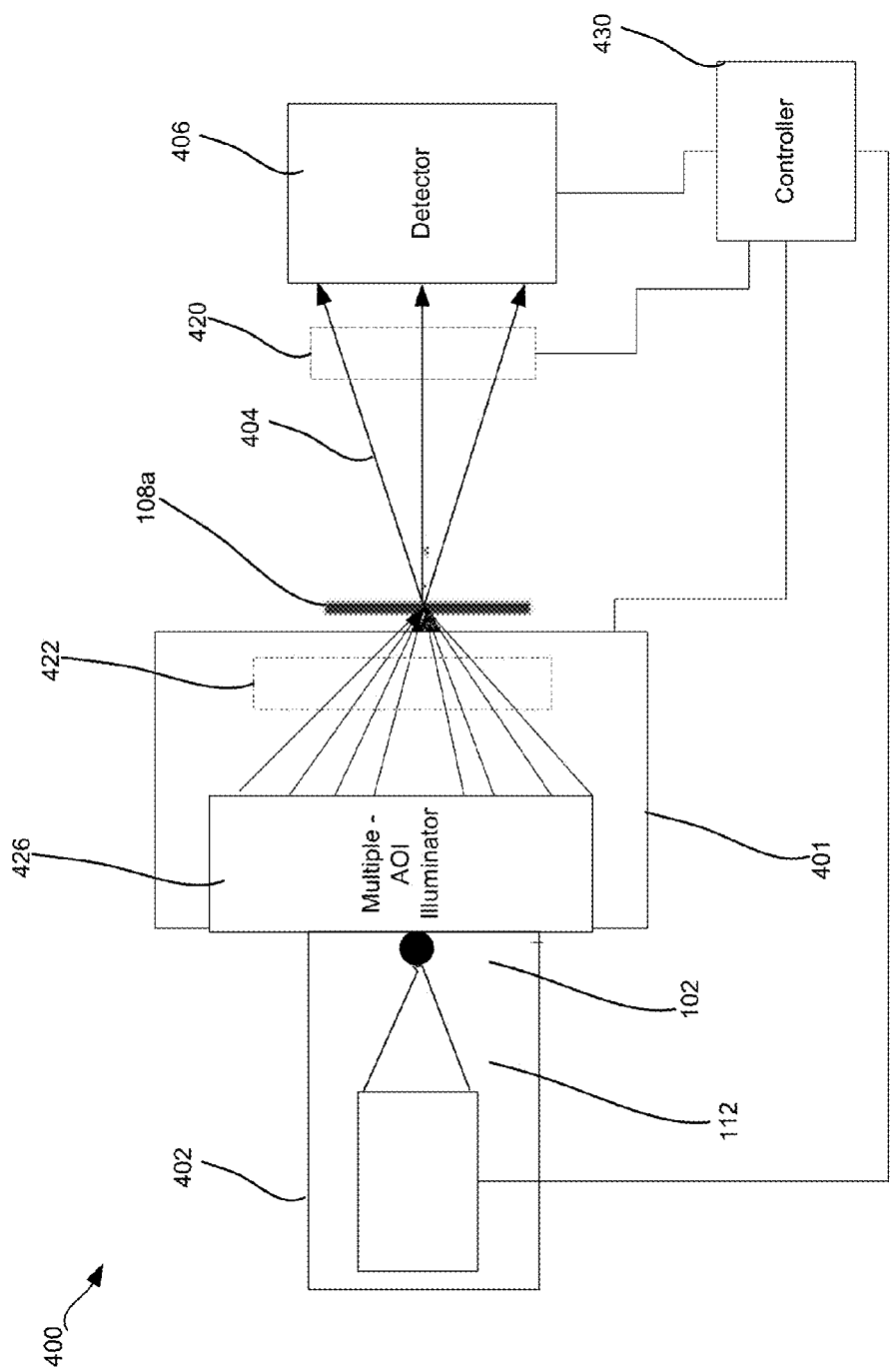
FIG. 4 is a diagrammatic representation of a transmission small angle x-ray scattering (T-SAXS) metrology system in accordance with one embodiment of the present invention.

FIG. 4 is a diagrammatic representation of SAXS metrology system 400 in accordance with one embodiment of the present invention. The system 400 may include any suitable illumination system 401 for producing x-rays with multiple AOI's, such as the illumination system of FIG. 1. Additionally, the SAXS system 400 may include one or more high brightness x-ray sources 402, including anode 112, with suitable x-ray photon energies for generating the X-rays that are incident on the sample (e.g., via the grazing mirrors). A high brightness x-ray source may include a solid anode X-ray source, a liquid metal jet X-ray source, and liquid droplet X-ray source, or other bright x-ray sources such as an Inverse-Compton x-ray source.

Figure 5:
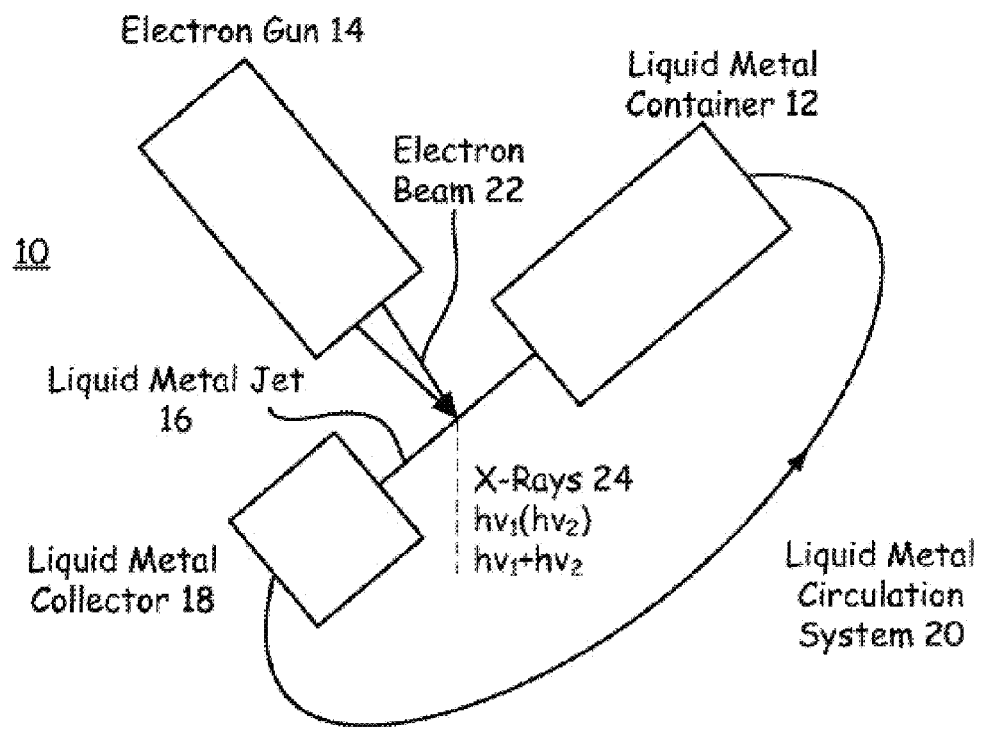
FIG. 5 is a diagrammatic representation of a liquid metal jet x-ray source.

Example embodiments of a liquid metal jet X-ray source are described is U.S. Pat. No. 7,929,667, which is incorporated herein by reference in its entirety. One embodiment of a liquid metal jet x-ray source 10 according to the present invention is depicted in FIG. 5. This source 10 includes a liquid metal container 12 and a microfocused electron gun 14. The liquid metal container 12 is equipped with a heating unit that provides an amount of thermal energy that is sufficient to melt a metal or combination of metals, producing a stream 16 that functions as the x-ray anode. Example methods for liquefying the metal include heating by electric, electromagnetic, thermal, and microwave heating mechanisms. This liquid metal container 12 may also be equipped with a pressurized unit to generate the liquid metal jet 16 through a nozzle. The pressure and nozzle size and shape are optimized for different metals, so as to achieve the desired x-ray source performance.

A liquid metal circulation system 20 transfers the liquid metal from a liquid metal collector 18 back to the liquid metal container 12. The electron gun 14 accelerates an electron beam 22 at an appropriate angle towards the liquid metal jet 16, thereby generating an x-ray beam 24. Because heating is less of an issue with this configuration, the electron beam 22 can be continuously fired at the liquid metal jet 16, thereby producing an x-ray beam 24 that is similarly continuous, at least during the measurement time as desired. Alternatively, a pulsed operation may be utilized, but is not preferred.

The photon energy and peak wavelength of the x-ray beam 24 that is generated is governed at least in part by the materials 10 that are selected for the liquid metal jet 16. For example, some relatively low melting-point metals are listed in Table 2 below, with the x-ray photon energy that is produced and fluorescence yield by its sub-shells.

TABLE 2

X-ray liquid metal anode materials with emission line x-ray energy and the Fluorescence yields for K, L shells.

| Element | Gallium | Indium | Tin | Thallium | Bismuth |
|---|---|---|---|---|---|
| Atomic No. | 31 | 49 | 50 | 81 | 83 |
| Melting T (° C.) | 30 | 156.8 | 232.1 | 304 | 271.6 |
| $K_a$(eV) | 9251.7 | 24210 | 25271 | N/A | N/A |
| $L_a$(eV) | N/A | N/A | N/A | 10269 | 10839 |
| Fluorescence Yield $\omega_k \times 10^{-1}$ | 5.4 | 8.4 | 8.7 | N/A | N/A |
| Fluorescence Yield $\omega_L \times 10^{-1}$ | N/A | N/A | N/A | 3.5 | 3.7 |

Some embodiments of the present invention may generate x-rays with photons having different energy levels and peak wavelengths, by using a mixture of two or more liquid metals as the anode. For example, by using a mixture of gallium and indium in the liquid metal anode 16, the x-ray source will simultaneously generate a beam 24 with some photons having an energy of about nine thousand eV due to the gallium, and some photons with an energy of about twenty-four thousand eV due to the indium. Further, the beam will have two distinct peak wavelengths, one attributable to the gallium and the other attributable to the indium. These peaks are superimposed on a background of continuum Bremsstrahlung radiation that is generated when high-energy electrons strike a metal target.

The balance between photons of different energy and wavelength can be controlled, at least in part, by the ratio of liquid metals in the anode 16. A source with two metals would then produce an x-ray beam having two distinct peak lines, and not a beam with a broad range of photon energies or wavelengths. Thus, a single x-ray source can be highly tailored to two specific applications. Of course, using three metals will produce a beam with three peak lines, and can be tailored to three specific applications, and so forth. It is understood that, in some cases, a single metal is also capable of producing multiple emission lines depending on the electronic structure of the metal used for the liquid jet.

X-ray scattering typically results in high contrast images which correspond to the difference in the densities of the structure materials. However, certain target structures may result in low density contrast, such as certain multilayer photoresist material. Another improvement involves tailoring the x-ray illumination wavelength to match absorption edges of the materials in the target. Studies have shown that contrast in x-ray scattering can be enhanced by tuning the illumination spectra to absorption peaks of the materials in the target so that one material absorbs more x-rays than another material to thereby increase contrast between such materials. For transmission based CD-SAXS applications, x-ray energies between 10 and 11 keV may work well, and result in illuminating targets whose structures contain high-z elements that have such absorption peaks at this range of energy levels, such as Hafnium or Tungsten. For solid metal or liquid metal jet illumination sources, the source has the highest flux in narrow energies bands associated with shell excitations of the constituent elements in the metal anode, commonly called characteristic radiation. Outside these peaks, a much lower level of flux is seen to be associated with bremsstrahlung, commonly called continuum radiation.

To increase the flux at the absorption peaks of interest, the solid metal or liquid metal jet anodes may be doped with elements that have excitation peaks at or near the desired absorption peaks of the target. This doping may be accomplished by adding a relatively small amount of material of a given element to the solid metal matrix or to the liquid metal used as the X-Ray anode. The anodes may also be doped with not merely one, but many elements, such that the peaks for any given source are distributed at many or all of the desired absorption wavelengths. Conversely, it may be possible on separate tools to dope the anodes with different materials so that each tool is utilized to probe a specific material in the target. Furthermore, by combining the scattering data from multiple wavelengths, it may be possible to resolve more parametric information about the target with greater precision.

Tuning the spectra of the anode to absorption edges of the target via doping has the effect of producing a greater scattered photon flux, which can ultimately reduce the length of measurement time that may be necessary to measure the critical dimension of a given target with a desired degree of precision.

Using a liquid metal x-ray source, it is possible to create a spot with a brightness that is around 1 order of magnitude greater than what may be available from a solid metal anode x-ray tube. For example, a liquid gallium x-ray source has a brightness in the range of about $10^{9-10}$ photons sec$^{-1}$ mm$^{-2}$ mrad$^{-2}$, as opposed to a brightness upper limit of about $10^{8-9}$ photons sec$^{-1}$ mm$^{-2}$ mrad$^{-2}$ for solid anodes of copper or molybdenum. With such a significant brightness gain, the x-ray spot size can be from about ten microns to about fifteen microns in diameter with a higher signal-to-noise ratio (SNR) than that of other sources, or have an even smaller spot size with a SNR that is still better than or equal to other sources.

In the illustrated embodiment of FIG. 4, the x-ray beams may be collected and reflected or refracted by a multiple-AOI illuminator 426 to produce multiple ranges of AOI's on the sample 108a. The multiple-AOI illuminator 426 may take any suitable form, such as the multiple grazing incident mirrors of FIG. 1 or other illumination embodiments described below.

The scattered x-rays 404 are collected by an x-ray detector 406, while a sample handler holds the sample 108a and translates, as well as rotates, the sample 108a for positioning and alignment and to produce angularly resolved scattered x-rays 404. However, since the multiple-AOI illuminator 426 provides multiple AOI's simultaneously, the sample does not need to be tilted to achieve different AOI's (sequentially). As a result, the illumination and collection sides of system 400 are arranged to together, provide incident x-rays and collect and detect scattered x-rays at multiple, simultaneous AOI's to thereby achieve significant improvement in throughput.

The multiple-AOI illuminator 426 can also be configurable to particular AOIs based upon the expected sample characteristics. For instance, complicated FinFET structures may require many AOIs spanning a large range from +45° to −45°, while other simpler structures may only require three or four specific AOIs for proper characterization. The multiple-AOI illuminator 426 and any associated components 422, such as pinholes or apertures, can be computer controlled (e.g., via controller 430) and enable the ability to choose AOIs based upon the sample characteristics.

The detector can be any suitable sensor for detecting scattered x-rays and generating a resulting spectra or image. By way of examples, the sensor can include one or more of the following: a photodiode array, a Charged Coupled Device (CCD), image plate, a hybrid pixel CCD, etc. The detector generally produces an intensity signal that can then be converted to an image by the detector (or controller 430).

Figure 6:
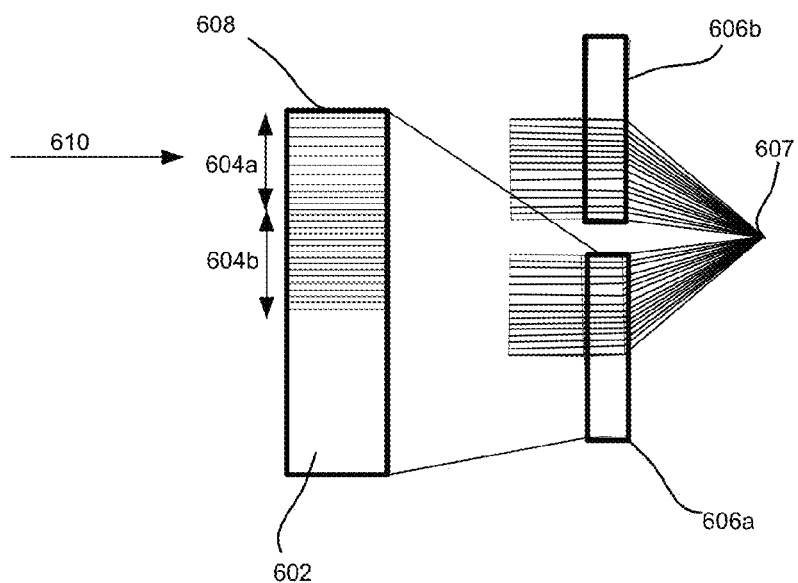
FIG. 6 is a diagrammatic representation of a Laue lens illumination configuration for a T-SAXS metrology system in accordance with an alternative embodiment of the present invention.

It should be noted that the T-SAXS illumination system (e.g., 401) configuration described above is not limited to using multiple multilayer grazing incident X-ray optics to collect and reflect multiple AOIs in parallel. The optics may include multilayer Laue lenses, as shown in FIG. 6. Laue lenses have multilayer coatings which achieve very high aspect ratio zones of variable period which are able to focus hard x-rays to very small spots. As shown in FIG. 6, element 608 is an enlargement of lens 606a which is also paired with lens 606b. Each lens half is formed from a plurality of layers that disposed over a substrate 602, such as Si. The multiple layers include thin layers 604b and thick layers 604a. A Laue lens is a set of specifically oriented crystals that focus x-ray photons via Bragg diffraction in a transmission configuration (the Laue geometry). The x-rays beams are refracted differently by the different spacings and focused to point 607.

Other multiple-AOI illuminator embodiments may include multiple Fresnel zone plate lenses or polycapillary optics to produce multiple beams at different AOIs. In principle, any type of optics (such as Bragg-Fresnel lenses, curved crystals, Wolter optics, etc.) can be employed to achieve different AOIs. An x-ray zone plate may be formed by concentric circles of interleaved material and air to refract x-rays to a focus point at multiple AOIs. By way of an implementation example, multiple capillary x-ray optics or zone plates can be aligned around one or more x-ray sources to produce a number of collimated beams that simultaneously interact with the sample.

The illumination optics (e.g., 401) of the systems described herein can be configured to optimize beam divergence and/or spectral purity for different target structures.

Figure 7A:
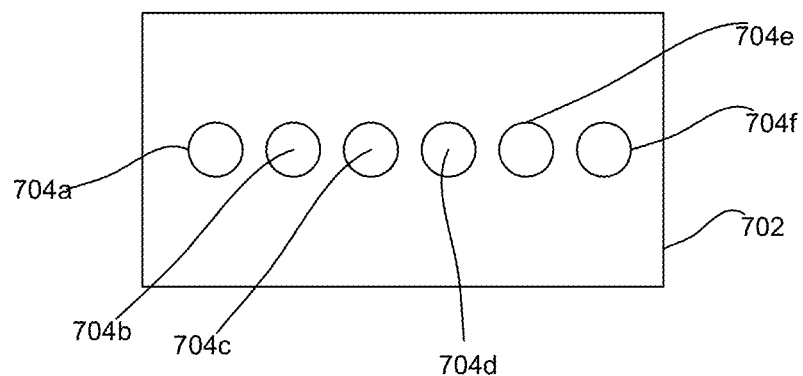
FIG. 7A is a diagrammatic representation of a diffraction pattern on a detector formed from low divergent beams.
Figure 7B:
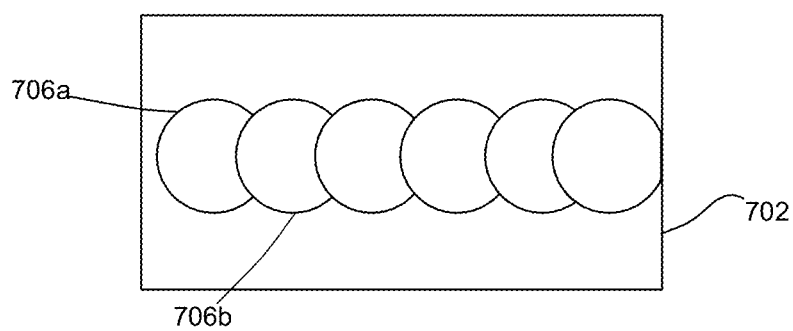
FIG. 7B illustrates a diffraction pattern formed from high divergent beams.

FIG. 7A is a diagrammatic representation of a diffraction pattern (704a-704f) formed from low divergent beams on a detector 702. In contrast, FIG. 7B illustrates a diffraction pattern (e.g., 706a and 706b) formed from high divergent beams. In this later example, the different diffraction orders may not be resolvable.

There are two factors that affect how much the diffraction orders overlap on the detector: spectral purity and beam divergence. Spectral purity is generally how monochromatic the wavelength range is ($\Delta\lambda/\lambda$). Sometimes the spectral purity can be relaxed, as long as the orders can still be resolved. Beam divergence relates to how much the beam is columnated. Optics that relax the spectral purity of the beam can be used for small pitch structures in which the peaks of the scattered signal are far from each other and the risk of peak overlap is decreased. Likewise, optics that relax the divergence of the beam can be used for small pitch structures in which the peaks of the scattered signal are far from each other and the risk of peak overlap is decreased.

Figure 7C:
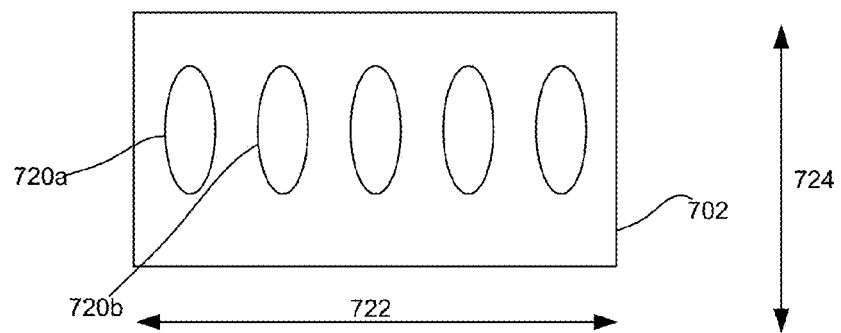
FIG. 7C shows the results for low divergence in a single axis and large divergence in an orthogonal axis.

X-ray optics with low divergence in a single axis and a very large divergence in an orthogonal axis can be used for a 2D structure that only scatters in a single axis (e.g., an array of lines). FIG. 7C shows the results for low divergence in a single axis 722 and large divergence in an orthogonal axis 724. This low and high divergence arrangement may also be possible for 3D structures, in which the axis of large divergence does not cause any peak overlapping. Relaxing the beam divergence for one direction allows relaxation of requirements of the optics so that the solid collection angle can be larger (since spots can be larger) and can collect more light. In contrast, a grid of structures, such as pinholes, may require low beam divergence in the two orthogonal directions of the grid. In addition, x-ray apodizers (e.g., 422 of FIG. 4) can be used, which can allow for resolving of partially overlapping peaks from different beams of different AOI.

Other aspects of the illumination system 401 can include multiple $0^{th}$ order beam blocks (e.g., 420 of FIG. 4), which can be computer controlled and modular. In some cases, the $0^{th}$ order scattering can have a large associated brightness that may damage the detector if not blocked. The illumination system can include differently sized and shaped blocks for specific applications when different x-ray optics produce beams of varying spot size and divergence. For instance, in the case in which the x-ray optics have low divergence in a single axis and a very large divergence in an orthogonal axis, the $0^{th}$ order beam block, rather than being circular and symmetric, could be rectangular or ellipsoidal, in order to compensate for the beam that has a low divergence in one axis and a large divergence in the other. Likewise, when multiple beams at different AOIs are incident on the wafer in parallel, multiple beam blocks would be used, with each $0^{th}$ order beam block having the proper size and shape to block its particular beam. Different block sizes and shapes can be moved in and out (or rotated in and out) of the $0^{th}$ order beam path, depending on the beam optics configuration. Each block may be formed from a material that substantially blocks the $0^{th}$ order beam. Example materials include lead and tungsten.

Figure 8:
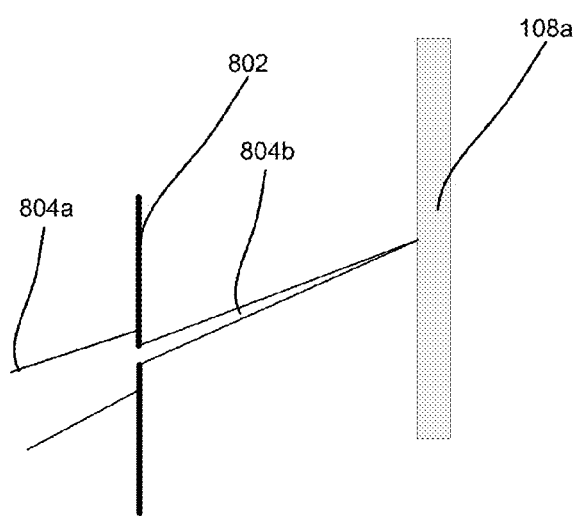
FIG. 8 is a diagrammatic representation of a portion of a pinhole system for controlling divergence in accordance with one embodiment of the present invention.

Other improvements include different sized pinholes for the beams at different AOIs to keep the spot size the same or control beam divergence for the different angles of incidence, and these pinholes can also be computer controlled and modular. For instance, in the case where x-ray optics with low divergence in a single axis and a very large divergence in an orthogonal axis are used, the pinholes, rather than being circular and symmetric, could be rectangular or ellipsoidal, in order to compensate for the beam which has a low divergence in one axis and a large divergence in the other. Likewise, when multiple beams at different AOIs are incident on the wafer in parallel, multiple sets of pinholes would be used, with each set of pinholes having the proper size and shape to produce the desired beam size and divergence for its particular beam. FIG. 8 is a diagrammatic representation of a portion of a pinhole system for controlling divergence in accordance with one embodiment of the present invention. As shown, an incident beam 804a having a divergence size is conditioned by aperture 802 to produce a smaller divergence size in the incident beam 804b. Pinholes placed close to the illumination optics (422) can be used to control divergence, while pinholes close to the sample (420) can be used to control spot size. Slits (e.g., 4 jaw slits), rather than just pinholes, can be used in the system 400.

Scatterless pinholes or apertures in which a single crystal is bonded to the edges of the pinholes or apertures can be used to reduce parasitic scattering of the beam. This pinhole arrangement can reduce the background noise of the SAXS measurements, increasing the signal to noise and thereby increasing the throughput. A calibration sample, such as Glassy Carbon, or simply a photon counting detector can be utilized to get the absolute photon count on the sample. The calibration results can be used to obtain scattering intensity curves on an absolute scale, rather than a relative scale, which can in certain instances improve the fitting and improve the precision and accuracy of certain geometric parameters. The x-ray intensity calibration can be accomplished using a photodiode or other detector mounted into the pinholes or apertures. Likewise, the x-ray intensity calibration can be accomplished using a photodiode or other detector mounted into the $0^{th}$ order beam block.

Different sized or types of pinholes can be dynamically switched into the illumination and/or collection path. In one example, the illumination optics are designed to have an arrangement that results in an upper limit of divergence and spot size. Pinhole or aperture structures can then be used to block portions of the illumination beams so as to achieve lower divergence beams and smaller spots sizes for particular target structures.

Figure 9:
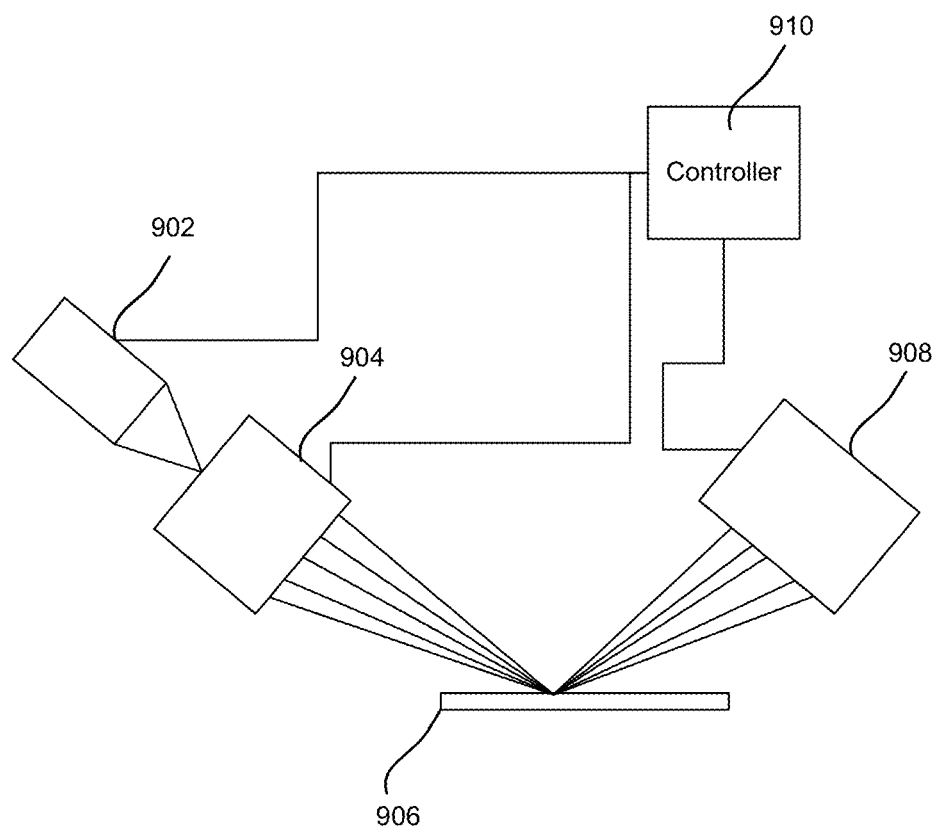
FIG. 9 is a diagrammatic representation of a grazing incidence small-angle x-ray scattering (GI-SAXS) system in accordance with an alternative embodiment of the present invention.

It should be noted that while the illumination and collection systems are described herein with respect to transmission SAXS, this does not preclude the use of these same illumination and collection systems for use with Grazing Incidence SAXS (GI-SAXS) for semiconductor metrology. FIG. 9 is a diagrammatic representation of a GI-SAXS system in accordance with an alternative embodiment of the present invention. As shown, an x-ray source 902 generates x-rays that are collected and reflected/refracted by illumination optics 904 onto the sample 906 at multiple AOIs. X-rays are scattered from the sample 906 onto detector 908. The system also includes a controller 910 for controlling the various components of the GI-SAXS system.

The GI-SAXS system can include multiple sets of optics, pinholes, slits, detectors, and beam blocks that are each optimized for different energies. Since GI-SAXS, in contrast to T-SAXS, does not need higher energy x-rays to penetrate the wafer substrate, x-ray sources with multiple energies, including lower energies, could be used such as liquid metal alloys of Indium Gallium and Tin.

Figure 10:
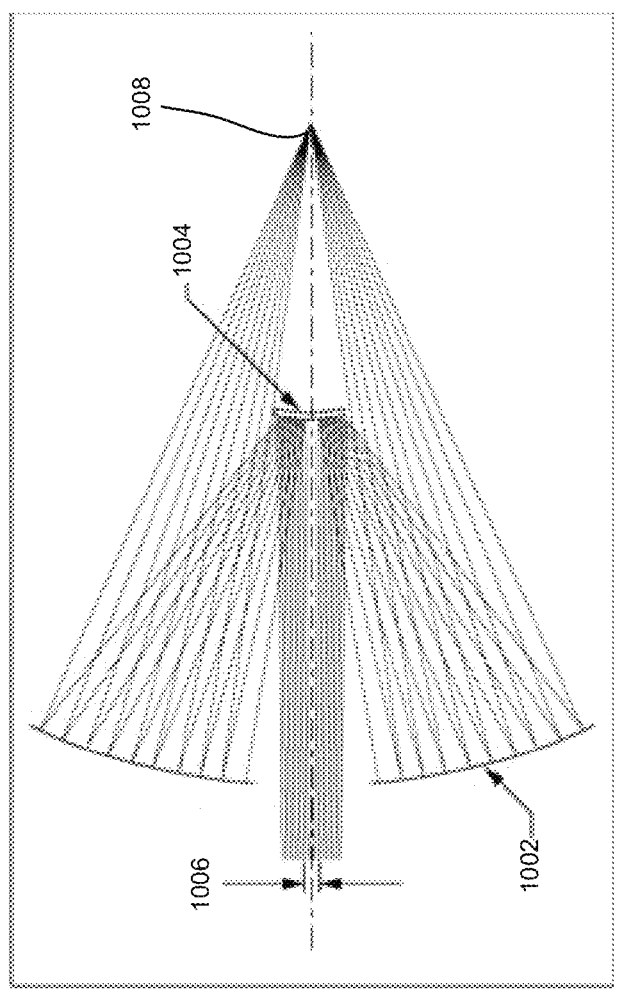
FIG. 10 illustrates a Schwarzschild objective with high reflectivity in accordance with another embodiment of the present invention.

In another embodiment, curved crystals can be used. Crystalline lattice planes can be chosen (such as <111>, <222>, <333> etc.), which provide much smaller periods (d), than are available with multilayer materials. With these much smaller periods, the reflectivity at larger angles of incidence is increased. At very small crystalline lattice parameters, angles of incidence much closer to normal can produce high reflectivity. Two curved crystals with the appropriately chosen lattice planes could be formed to produce a Schwarzschild objective with high reflectivity at x-ray energies of 15 keV (FIG. 10). As shown, a primary crystalline mirror 1004 receives x-rays and refracts them to secondary crystalline mirrors (e.g., 1002), which then refract the x-rays to a focus point 1008. A curved crystal Schwarzschild objective would increase the solid angle of collection over conventional x-ray optics, thus, increasing the photon flux on the sample and increasing the throughput.

For instance, in the case of cubic crystals the distance between lattice planes, d, is given by:

$$\frac{1}{d^2} = \frac{h^2 + k^2 + l^2}{a^2}$$

where h, k, and l are the Miller indices and a is the lattice constant of the crystal. For Silicon with a lattice constant of 5.43 Å, the d-spacing of the <333> plane is 1.045 Å. For a conventional x-ray source such as Mo kα, the wavelength λ is 0.71 Å. Using this wavelength in the Bragg formula:

$$\lambda = 2d \sin \theta$$

with the d-spacing of 1.045 Å, the first Bragg reflection is at 19.86°. Likewise Chromium has a lattice constant of 2.91 Å, giving the d-spacing of the <333> plane a value of 0.56 Å and a Bragg angle of 39.34° for the same case of Mo kα adiation. In this case, the <333> plane of Silicon or Chromium could be grown epitaxially on a curved substrate, or on a flat substrate which is then curved.

In sum, different crystal materials with different lattice plane orientations could be used to provide different d spacings and resulting AOIs for particular wavelengths. Accordingly, this type of crystalline illumination system can be used for optical systems with large acceptance angle ranges.

Figure 11:
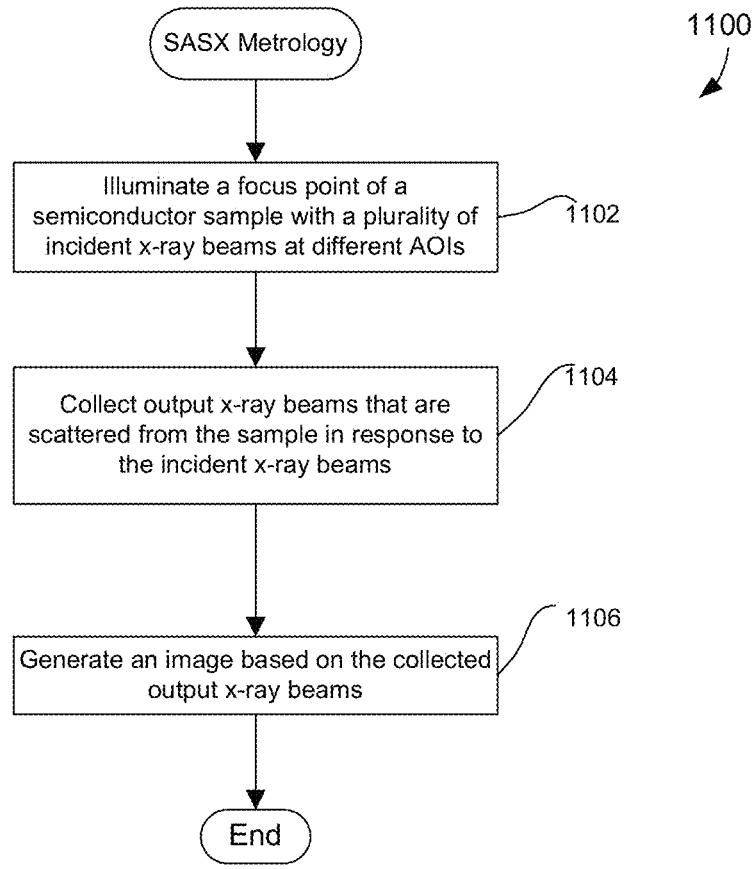
FIG. 11 is a flow chart illustrating a procedure for performing SAXS metrology in accordance with one embodiment of the present invention.

FIG. 11 is a flow chart illustrating a procedure 1100 for performing SAXS metrology in accordance with one embodiment of the present invention. Initially, a focus point of a semiconductor sample may be illuminated with a plurality of incident x-ray beams in operation 1102. For example, any of the illumination systems described herein may be used to produce multiple AOI beams. Output x-ray beams that are scattered from the sample in response to the incident x-ray beams may then be collected in operation 1104. An image (or signal) may then be generated based on the collected output x-ray beams in operation 1106.

Certain embodiments of the present invention allow multiple x-ray optics aligned around the source to produce a plurality of of collimated beams which simultaneously interact with the sample at different angles of incidence, which allows for higher throughput. The use of multiple x-ray optics around the source also increases the overall collection solid angle and, likewise, the use of multiple x-ray optics can produce multiple x-ray beams at different angles of incidence which interact with the sample in parallel rather than in series.

It should be recognized that the various steps described throughout the present disclosure may be carried out by a controller (e.g., 430 of FIG. 4), such as single processor system or, alternatively, a multiple processor system. Moreover, different subsystems of the system may include a computer system suitable for carrying out at least a portion of the steps described herein. Therefore, the aforementioned description should not be interpreted as a limitation on the present invention but merely an illustration. Further, the one or more controller system may be configured to perform any other step(s) of any of the method embodiments described herein.

In addition, the controller system may be communicatively coupled to a detector system in any manner known in the art. For example, the controller system may be coupled to computing systems associated with the detector system. In another example, the detector system may be controlled directly by a single computer system coupled to the controller system.

The controller system of the metrology system may be configured to receive and/or acquire data or information from the subsystems of the system by a transmission medium that may include wireline and/or wireless portions. In this manner, the transmission medium may serve as a data link between the controller system and other subsystems of the system.

The controller system of the metrology system may be configured to receive and/or acquire data or information (e.g., measurement spectra or images, statistical results, reference or calibration data, training data, models, extracted features or transformation results, transformed datasets, curve fittings, qualitative and quantitative results, etc.) from other systems by a transmission medium that may include wireline and/or wireless portions. In this manner, the transmission medium may serve as a data link between the controller system and other systems (e.g., memory on-board metrology system, external memory, reference measurement source, or other external systems). For example, the controller system may be configured to receive measurement data from a storage medium (e.g., internal or external memory) via a data link. For instance, spectral results obtained using the detection system may be stored in a permanent or semipermanent memory device (e.g., internal or external memory). In this regard, the spectral results may be imported from on-board memory or from an external memory system. Moreover, the controller system may send data to other systems via a transmission medium. For instance, qualitative and/or quantitative results determined by processor system may be communicated and stored in an external memory. In this regard, measurement results may be exported to another system.

The controller system may include, but is not limited to, a personal computer system, mainframe computer system, workstation, image computer, parallel processor, or any other device known in the art. In general, the term "processor system" may be broadly defined to encompass any device having one or more processors, which execute instructions from a memory medium. Program instructions implementing methods such as those described herein may be transmitted over a transmission medium such as a wire, cable, or wireless transmission link. Program instructions may be stored in a computer readable medium (e.g., memory). Exemplary computer-readable media include read-only memory, a random access memory, a magnetic or optical disk, or a magnetic tape.

Computational algorithms are usually optimized for metrology applications with one or more approaches being used such as design and implementation of computational hardware, parallelization, distribution of computation, load-balancing, multi-service support, dynamic load optimization, etc. Different implementations of algorithms can be done in firmware, software, FPGA, programmable optics components, etc.

The data analysis and fitting steps may be used to pursue one of the following goals: measurement of CD, SWA, shape, stress, focus/dose, overlay, and/or any combination thereof; modeling and/or design of metrology systems; and modeling, design, and/or optimization of metrology targets.

Certain embodiments of the present invention presented here generally address the field of semiconductor metrology and process control, and are not limited to the hardware, algorithm/software implementations and architectures, and use cases summarized above.

Although the foregoing invention has been described in some detail for purposes of clarity of understanding, it will be apparent that certain changes and modifications may be practiced within the scope of the appended claims. It should be noted that there are many alternative ways of implementing the processes, systems, and apparatus of the present invention. For example, the techniques can be applied to other types of samples, beside semiconductor wafers, such as reticles. Accordingly, the present embodiments are to be considered as illustrative and not restrictive, and the invention is not to be limited to the details given herein.

What is claimed is:

1. A semiconductor metrology system, comprising:
an x-ray source for generating x-rays;
illumination optics for collecting and reflecting or refracting a particular cone portion of the generated x-rays towards a particular focus point on a semiconductor sample in the form of a plurality of incident beams at a plurality of different angles of incidence (AOIs), wherein the illumination optics comprise a plurality of separate grazing incident reflecting mirrors, wherein the grazing incident reflecting mirrors comprise sets of one or more grazing incident reflecting mirrors having multiple layers and each set is arranged and sized to collect and reflect a specific solid cone of angles of the generated x-rays at the plurality of different AOIs, wherein each grazing incident reflecting mirror has a curved shape and the grazing incident reflecting mirrors form nested and separated rings so that each ring collects and reflects a different range of AOI's;
a sensor for collecting output x-ray beams that are scattered from the sample in response to the incident beams on the sample at the different AOIs; and
a controller configured for performing the following operations:
controlling operation of the x-ray source and illumination optics; and
receiving the output x-rays beams and generating an image from such output x-rays.

2. The system of claim 1, wherein the illumination optics and sensor are arranged to form a transmission small-angle x-ray scattering (T-SAXS) system.

3. The system of claim 1, wherein the illumination optics and sensor are arranged to form a grazing incident small-angle x-ray scattering (GI-SAXS) system.

4. The system of claim 1, wherein the multiple layers of the grazing incident reflecting mirrors each have a plurality of portions having different periods, which is each selected to meet the Bragg condition so that the incident beams that are collected and reflected by all the portions are directed towards the particular focus point.

5. The system of claim 1, wherein the illumination optics are configured to reflect or refract the plurality of incident beams simultaneously from at least one $2\pi$ cone portion towards the sample at the different angles of incidence (AOIs).

6. The system of claim 1, wherein the x-ray source comprises an anode that is doped with one or more elements.

7. The system of claim 1, wherein the illumination optics further comprise:
a multi-AOI illuminator having the grazing incident reflecting mirrors for collecting and reflecting or refracting the incident beams towards the particular focus point on the sample at the different AOIs; and
a plurality of differently sized apertures placed in a path of the incident beams to control a spot size and/or beam divergence for the different AOIs.

8. The system of claim 7, wherein at least one of the apertures each include a single crystal that is bonded to edges of such aperture.

9. The system of claim 7, wherein each of the differently sized apertures are arranged to be dynamically positioned in a path of the incident beams or output x-ray beams, wherein the multi-AOI illuminator is arranged to cause the incident beams to have an upper limit of a first divergence and first spot size and the differently sized apertures are sized and shaped to block portions of the incident beams so as to achieve lower divergence than the first divergence and smaller spots sizes than the first spot size for particular target structures.

10. A semiconductor metrology system, comprising:
an x-ray source for generating x-rays; and
illumination optics for collecting and reflecting or refracting a portion of the generated x-rays towards a particular focus point on a semiconductor sample in the form of a plurality of incident beams at a plurality of different angles of incidence (AOIs), wherein the illumination optics comprise a plurality of separate grazing incident reflecting mirrors, wherein the grazing incident reflecting mirrors comprise sets of one or more grazing incident reflecting mirrors having multiple layers and each set is arranged and sized to collect and reflect a specific solid cone of angles of the generated x-rays at the plurality of different AOIs, wherein the grazing incident reflecting mirrors are arranged in a plurality of positions in a plurality of nested rings so that the grazing incident reflecting portions in each ring together collect and reflect a different range of AOI's than grazing incident reflecting portions in other rings.

11. A method of measuring small-angle x-ray scattering from a semiconductor sample, the method comprising:
in a small angle x-ray scattering (SAXS) system, illuminating a focus point of a semiconductor sample with a plurality of incident x-ray beams at a plurality of different angles of incidence (AOIs), wherein the different AOIs are produced simultaneously on the focus point of the sample from illumination optics for collecting and reflecting or refracting a particular cone portion as the plurality of incident x-ray beams towards the focus point, wherein the SAXS system comprises sets of one or more grazing incident reflecting mirrors having multiple layers and each set is arranged and sized to collect and reflect a specific solid cone of angles of the x-ray beams at the plurality of different AOIs, wherein each grazing incident reflecting mirror has a curved shape and the sets of grazing incident reflecting mirrors form nested and separated rings so that each ring collects and reflects a different range of AOI's;
in the SAXS system, collecting output x-ray beams that are scattered from the sample in response to the incident beams on the sample at the different AOIs; and
in the SAXS system, generating an image based on the output x-ray beams.

12. The method of claim 11, wherein the SAXS system is a transmission SAXS system.

13. The method of claim 11, wherein the SAXS system is a grazing incidence SAXS system.

* * * * *